United States Patent
Esch et al.

(10) Patent No.: US 6,214,383 B1
(45) Date of Patent: Apr. 10, 2001

(54) PRECIPITATED SILICAS WHICH CONTAIN AN ACTIVE SUBSTANCE

(75) Inventors: Heinz Esch, Bonn-Duisdorf; Robert Kuhlmann, Erftstadt; Matthias Neumüller, Hasselroth; Karin Otto, Bonn; Ralf Rausch, Kreuzau; Klaus-Peter Thomas, Wölfersheim, all of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/208,453

(22) Filed: Dec. 10, 1998

(30) Foreign Application Priority Data

Dec. 10, 1997 (DE) ............................. 197 54 798
Jan. 28, 1998 (DE) ............................. 198 03 066

(51) Int. Cl.$^7$ ............................. A61K 9/14; A61K 7/18
(52) U.S. Cl. ............................. 424/489; 424/49; 424/52
(58) Field of Search ............................. 424/489, 490, 424/464, 49, 52; 428/404

(56) References Cited

U.S. PATENT DOCUMENTS

| | | |
|---|---|---|
| 4,172,121 | 10/1979 | Calvin . |
| 4,756,903 | 7/1988 | Shinpo et al. . |
| 5,413,844 | 5/1995 | Persello . |
| 5,635,214 | 6/1997 | Ponchon . |
| 5,698,327 | * 12/1997 | Persello ............................. 428/404 |

FOREIGN PATENT DOCUMENTS

| | | |
|---|---|---|
| 1 016 410 | 9/1957 | (DE) . |
| 689 09 113 | 3/1994 | (DE) . |
| 0 345 116 | 12/1989 | (EP) . |
| 0 575 137 | 12/1993 | (EP) . |

OTHER PUBLICATIONS

Official action of the Germany/European Patent Office dated Sep. 15, 1998.

* cited by examiner

*Primary Examiner*—James M. Spear
(74) *Attorney, Agent, or Firm*—Pillsbury Winthrop LLP

(57) ABSTRACT

A precipitated silica which contains an active substance with a characteristic, delayed release of active substance is prepared by adding the active substance during preparation of the precipitated silica. The precipitated silica containing the active substance may be added to oral hygiene agents such as toothpastes, topical fluoride preparations, dental materials or medicinal chewing gums.

7 Claims, 2 Drawing Sheets

PRECIPITATED SILICAS WHICH CONTAIN AN ACTIVE SUBSTANCE

FIELD OF THE INVENTION

The invention relates to precipitated silicas which contain an active substance, the preparation thereof and the use thereof in oral hygiene agents.

BACKGROUND OF THE INVENTION

Fluoride ions play a critical part in the prevention of caries. Thus, inter alia, fluoride ions are added to drinking water in order to counter the spread of caries.

Another way of using fluoride ions for combating caries is the use of toothpaste which contains fluoride ions (see "Oral Hygiene Products and Practice" by Morton Pader in "Cosmetic Science and Technology Series", vol. 6, pages 383 et seq. (1988), Marcel Dekker, Inc.). For this purpose, it is known that fluoride ions may be added to toothpastes in the form of NaF, MFP, aminofluoride, tin fluoride, etc. In addition, these toothpastes may contain precipitated silicas which have an abrasive and/or thickening effect (WO 93/24103). The availability of fluoride ions in the oral cavity, however, is substantially restricted to the short time during which the teeth are cleaned.

It is known that hydrofluoric acid can be added to an aqueous slurry of silica gel or xerogel. This slurry is then mixed with the components for preparing a toothpaste, wherein, inter alia, calcium chloride is also added (DE-A 24 16 742). Treatment with hydrofluoric acid causes Si—F bonds to be produced on the silica gel which means that cations, for example calcium ions, are adsorbed less by the silica gel. The formation of fluorine anions and their controlled release in a toothpaste is not described in the document DE-A 24 16 742.

It is known that pyrogenic silicon dioxide which contains 1 to 5% of adsorbed fluoride can be incorporated into toothpaste. This toothpaste always contains 800 to 1200 ppm of free fluoride which is available for appropriate therapeutic treatment (U.S. Pat. No. 4,172,121). The pyrogenic silicon dioxide in this toothpaste, in addition to providing a medium which contains fluoride ions, also acts as a thickening agent which provides the toothpaste with the requisite pasty consistency.

Pyrogenic silica which contains fluoride is prepared by treating pyrogenic silica with HF gas in accordance with U.S. Pat. No. 4,054,689.

It is known that precipitated silica which contains fluoride can be prepared by introducing sodium fluoride and oxalic acid into an aqueous recipient vessel and then precipitating the precipitated silica by simultaneous addition of sodium silicate solution and sulfuric acid (DE-B 12 93 138).

As a result of adding sodium fluoride and oxalic acid, iron ions are complexed in the precipitation mixture and a precipitated silica with a low concentration of iron is obtained. Adsorption of sodium fluoride on the precipitated silica does not take place.

A critical factor for improving the efficacy of oral hygiene preparations is regarded in particular as maintaining the concentration of active substance in the oral cavity for as long as possible after spontaneous release of the active substance. The objective is to improve retention of the active substance and thus also to produce the required effect with reduced amounts of active substance. Undesirable effects due to high concentrations should largely be avoided in this way.

Taking, as an example, the active substance fluoride, whose anticaries effect has been demonstrated in many clinical and epidemiological studies, it can be shown that the desired protection against caries can be produced even with extremely low concentrations (see Y. Ericson, J. Dent. Res. 59 (DII):2131 (1980); O. Backer Dirks, W. Künzel and J. P. Carlos, Caries Res. 12 (Suppl. 1):7 (1978); A. r. Volpe, in a textbook of Preventive Dentistry (R. C. Caldwell and R. E. Stallard, eds.), Saunders, Philadelphia, 1997, chap. 12).

Furthermore, there are indications that the frequency of fluoride application, i.e. the presence of fluoride ions at the correct time and in the correct place, in the event of acid attack is of greater importance than the fluoride concentration (see "Oral Hygiene Products and Practice" by Morton Pader in "Cosmetic Science and Technology Series" vol. 6, pages 383 et seq., (1988), Marcel Dekker, Inc.).

These findings led to the demand that research activity be directed towards maximising the time of action of fluoride while simultaneously minimising the fluoride concentration. Also, the toxicological aspects of increasing the fluoride doses or increasing the accumulation of fluoride, e.g. due to fluorinated drinking water, mouthwashes, toothpastes, topical fluoride preparations, fluoride tablets, etc., must not be ignored.

Again, in the case of active anti-plaque substances, it has been shown, by in vitro and in vivo studies, that the key to an improved effect is to be found in improved retention of the active substance. Thus, for example, exceptional plaque inhibition is produced by chlorhexidine which is attributed mainly to its retention in the oral cavity and gradual release from the plaque matrix and mucous membranes. A long-lasting antimicrobial effect was detected in early studies by determining the number of bacteria in saliva after rinsing out the mouth once (see K. Kornmann: Antimicrobial agents, in Loe, H & Kleinmann DV: Dental Plaque control measures and oral hygiene practices, Oxford/Washington, IRL Press, 121–142, 1986; P. Germo, P. Bonesvoll, G. Rolla: Relationship between plaque inhibiting effect and retention of Chlorhexidine in the oral cavity. Archs Oral Biol. 19:1031–1034, 1974; W.R. Roberts, M. Addy: Comparison of the bisguanidine antiseptics, alexine and chlorhexidine: i Effects on plaque accumulation and salivary bacteria. J. Clin. Periodontol. 8:8 213–219, 1981).

Another example is triclosan (2,4,4'trichloro-2'-hydroxydiphenyl ether), which has a distinct plaque-inhibiting effect only when combined with a copolymer (polyvinylmethylether/maleic acid) which improves the retention of triclosan (see American Journal of Dentistry, vol. 2, Special Issue, September, 1989: Report on the use of Triclosan/Copolymer Dentifrices in the Control of Plaque and Gingivitis).

It is known that silicas, as highly disperse substances, are able to be stored in fissures, micro-cracks and tubuli in the surface of teeth. The blocking of uncovered dentine tubuli in this way by silica leads to a desensitising effect (see M. Addy, P. Mostafa and R. Newcombe, Dentine Hypersensitivity: A Comparison of five toothpastes used during a six-week treatment period; British Dent. J. 163, 45–50, 1987).

There is, therefore, a need to provide a precipitated silica with the ability to carry active substances as oral hygiene agents, which satisfies all the requirements placed on this type of agent with regard to tolerance, abrasiveness, rheology, sensory and optical properties, and is also able to fix active substances in the oral cavity and then to release them in a controlled manner over a relatively long period of time.

SUMMARY OF THE INVENTION

The invention provides precipitated silicas which contain an active substance and which are characterized by a characteristic, delayed release of active substance.

The precipitated silica which contains an active substance may preferably be characterized by:
the concentration of active substance
the release dynamics of the active substance.

In a preferred embodiment, the precipitated silica according to the invention may have the following physicochemical parameters

| | | |
|---|---|---|
| Moisture % | 1–10, | preferably 1–7 |
| pH | 2.5–8.5, | preferably 6–8 |
| $N_2$ surface area $m^2/g$ | 25–800, | preferably 25–400 |
| Average particle size (Malvern) $\mu m$ | 2–100, | preferably 2–20 |

The invention also provides a process for preparing precipitated silica with the ability to carry an active substance according to the invention which is characterized in that a precipitated silica is prepared in a known manner, wherein an active substance which is moderately to sparingly soluble in water is placed either in the precipitation recipient vessel or in the precipitation suspension or is dried together with the washed and optionally redispersed precipitated silica paste or is milled simultaneously with the dried material.

The preparation of amorphous silicas is described in a variety of ways. The common feature of all the methods is the reaction of an alkali metal silicate solution with mineral acid or $Co_2$ while maintaining specific precipitating conditions, such as e.g. temperature, time, pH and solids content in the precipitation suspension. Then the pH is lowered by adding more acid. The mixture is stirred continuously during the precipitation and acidification phases. The suspension is filtered and the filter cake is washed, dried and milled.

Amorphous silicas according to the invention are prepared in such a way that a precipitated silica is prepared in a known manner, wherein an active substance which is moderately (0.1–1.0 molar) to sparingly (less than 0.1 molar) soluble in water either in the precipitation recipient vessel or in the precipitation suspension or is dried together with the washed and optionally redispersed silica paste or is milled simultaneously with the dried material.

Alkali metal fluorides, alkaline earth metal fluorides or fluoroapatite, for example, may be used as a component which contains fluoride ions, wherein fluorides from alkali metal compounds may also be bonded by adding alkaline earth metal ions. Further active substances may be: chlorhexidine, triclosan, hydroxyethane-1,1-diphosphonic acid, alkali metal pyrophosphates, zinc citrate, etc.

The precipitated silicas may be prepared in the ways described in the documents DE-A 44 23 493, DE-AS 14 67 019 and EP-B 0 272 380.

It has now been shown that a preferred form of preparation comprises placing the active substance in the precipitation recipient vessel or the spray dryer feed material. This ensures the most uniform and the finest distribution in the final product and the greatest retention effect. The therapeutically active amounts of fluoride are 0.001 to 10%, preferably 0.005 to 1.0%. The amount of triclosan is 0.1–1.0%, preferably 0.2–0.5%.

Any thickening, abrasive or bifunctional silica is suitable as a carrier silica. Synthetic, amorphous silicas are preferred, such as those described in EP 0 643 015 and obtainable from Degussa AG, Germany under the tradename SIDENT®. ZEODENT silicas from the J.M. Huber Corporation, Chemical Division, Havre de Grace, Md., TIXOSIL silicas from Rhone-Poulenc Chimie Les Mirroirs, La Defense 3 F-92400 Courbevoie, France; SORBOSIL silicas from Crosfield Chemicals, Warrington Cheshire, England or SYLOID silicas from Grace & Co., Davison Chemical Division, U.S.A. may also be used.

The precipitated silicas which are able to carry active substances according to the invention are preferably prepared by placing water and the active substance in a precipitation vessel, heating the mixture to a temperature of 50° to 100° C., preferably 80° to 90° C., adjusting the pH and the alkali metal concentration by adding sodium silicate solution while maintaining the temperature, and then adding sodium silicate solution and sulfuric acid, simultaneously, while keeping the pH and the alkali metal concentration constant, or one after the other, then acidifying to a pH of preferably 7 by adding further sulfuric acid, optionally stirring again, filtering, washing salt-free, redispersing the filter cake, drying with a spray dryer and milling the granular silica obtained.

The commercially available sodium silicate solution may have a concentration of, as a non-limiting example, 26.8% $SiO_2$ and 7.85% $Na_2O$ and a density of 1.352 g/ml.

The sulfuric acid may have a concentration of 50–96%.

Silicas according to the invention may be used in a conventional manner which is known to a person skilled in the art in oral hygiene preparations such as toothpastes, medicinal chewing gums and topical fluoride preparations as well as dental materials. In this case they may entirely or partly replace the silicas conventionally used there. A preferred area of use is in toothpastes. In addition, however, a combination with other, optionally soluble, active substances and the preparation of gel formulations etc., is also possible.

Dental care agents according to the invention containing (sic) one or more of the raw materials used according to the prior art, such as water, binders, such as e.g. cellulose derivatives such as carboxymethyl cellulose and their alkali metal salts, in particular sodium salts, hydroxyalkyl celluloses, xanthan gum, tragacanth gum, carragenates, alginates and gum arabica, etc., polishing substances (precipitated and pyrogenic silicas, dicalcium phosphate, chalk, aluminium hydroxide, etc.), moisture-retaining agents such as e.g. glycerol, sorbitol, propylene glycol, polyethylene glycols with low molecular weights, 1,4-butanediol, xylitol, etc., flavoring, surfactants such as e.g. alkyl sulfates, sodium lauryl sulfate, sarcosides, taurin fatty acid amides, monoglyceride sulfate, betains, etc., colorants and/or titanium dioxide, sweeteners, buffers, bases or acids, preservatives and active substances.

The dental care agents are prepared in accordance with the prior art. The ingredients, in a suitable form, are mixed, swollen and dispersed.

Precipitated silicas according to the invention may be used as an additive in toothpastes, in particular as a thickening and/or abrasive component which also releases active substances.

Precipitated silicas according to the invention have the following advantages:

Silicas according to the invention are used as a carrier for dentally active substances which are stored at the site of action and then release the active substance in small doses over a relatively long period of time (deposition effect, controlled release). The silicas thus act as active substance stores which contain the active substance in adsorbed, absorbed or chemisorbed form. Any form of silica, e.g. precipitated silicas or silica gels or pyrogenic silicas, may be used. Any sparingly soluble fluoride, such as e.g. $CaF_2$ and sparingly soluble active substance such as e.g. triclosan or chlorhexidine may be used as an active substance.

The sparingly soluble active substances may be combined with readily soluble active substances, such as e.g. NaF, monofluorophosphate, etc. and then targeted adjustment of the active substance release dynamics, that is a targeted combination of the immediate and the deposition effect, is possible. The advantages of the silicas according to the invention are based on the longer availability and thus improved therapeutic efficacy, e.g. improved prevention of caries due to improving the resistance of teeth to demineralization. This means that small doses of active substances are possible and fewer side effects or lower toxicity would be expected. The addition of fluoride to drinking water, i.e. the compulsory provision of a medicament, may become unnecessary.

This application is based on German Applications DE 19754 798.2, filed Dec. 10, 1997, and DE 19803 066.5, filed Jan. 28, 1998, the disclosures of which are incorporated herein by reference.

DETAILED DESCRIPTION OF THE PREFERRED EMBODIMENTS

EXAMPLES

Figure 1:
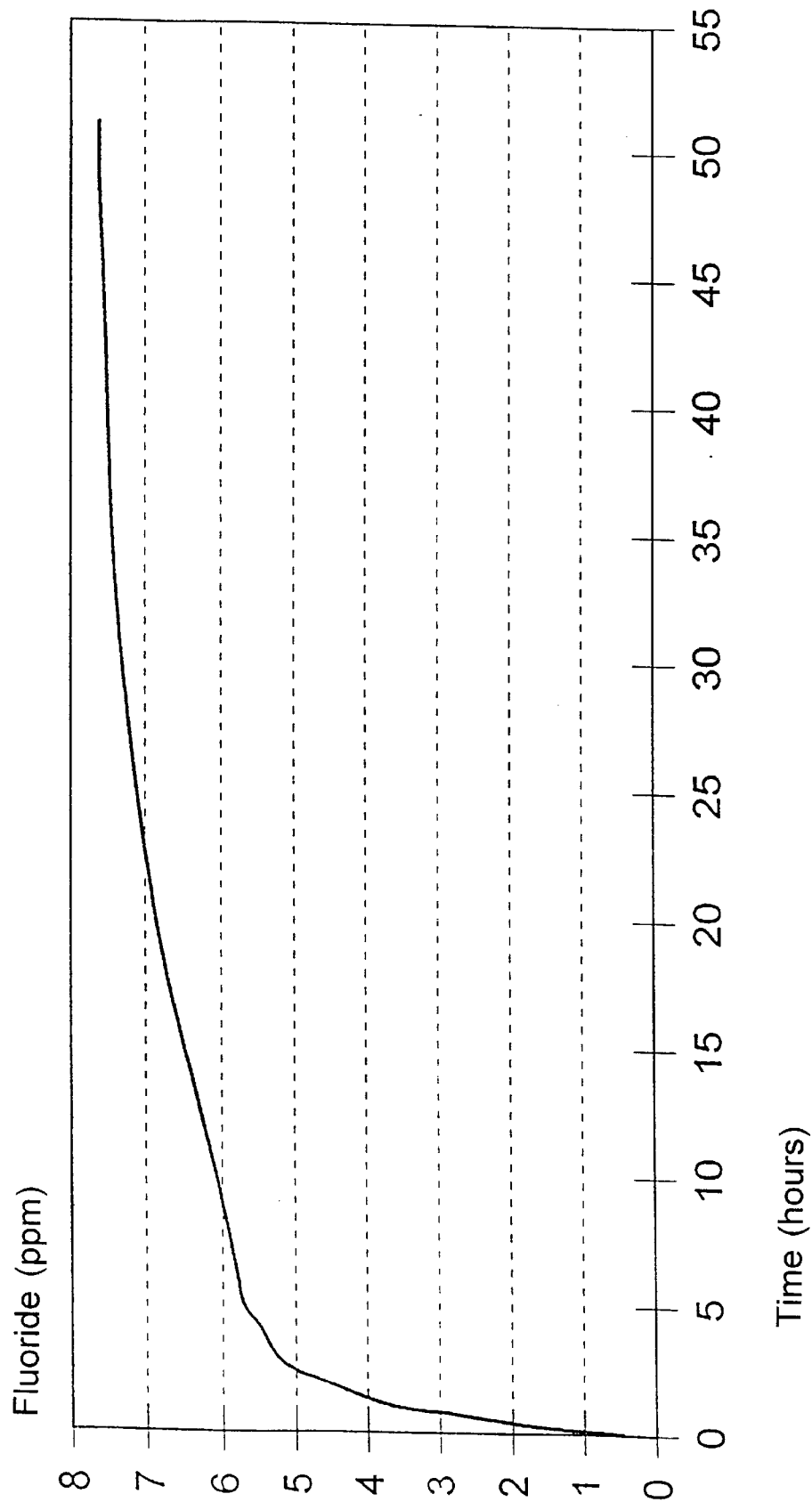
FIG. 1 shows, graphically, the relationship between fluoride concentration and time, for a silica according to Example 1.

Possible variants of the method for preparing precipitated silicas according to the invention are explained in the example relating to doping with fluoride:

Process Variant 1

Fluoride salts in the precipitation vessel +alkaline earth metal chlorides at the end of precipitation.

Process Variant 2

Fluoride salts +alkaline earth metal chlorides at the end of precipitation.

Process Variant 3

Fluoride salts in the precipitation vessel.

Process Variant 4

Fluoride salts in the spray dryer feed material.

Preparing Abrasive Precipitated Silicas which Contain Fluoride Ions

Example 1

(Fluoride-Containing Abrasive Silica)

Precipitation is performed substantially in accordance with DE-A 44 23 493, Example 1 with the addition of $CaF_2$ in the precipitation recipient vessel.

12.8 l of water and 52.8 g of $CaF_2$ are initially introduced, with stirring, into a 50 l precipitation vessel with indirect heating and then heated to 85° C. While maintaining this temperature, a pH of 8.5 is first set by adding a little sodium silicate solution (26.8% $SiO_2$ and 7.85% $Na_2O$, density 1.352 g/ml). Then precipitation is continued for 240 min by adding 60.0 ml/min of waterglass (composition as given above) and enough sulfuric acid (50% strength) to maintain a constant pH of 8.5. The suspension obtained is then acidified with sulfuric acid (50% strength) to a pH of ≦7.

The reaction mixture is stirred for a further 60 minutes, filtered, washed salt-free and dried in a spray dryer. The product is then milled.

The precipitated silica obtained has the following physico-chemical characteristics:

| | |
|---|---|
| Moisture % | 3.2 |
| pH | 8.0 |
| Conductivity $\mu S/cm$ | 400 |
| $N_2$ surface area $m^2/g$ | 31 |

| | |
|---|---|
| Mean particle size (Malvern) $\mu m$ | 10.2 |
| Fluoride ion concentration % | 0.5 |

Example 2

(Comparison Example, Fluoride-Free Abrasive Silica)

An abrasive precipitated silica was prepared in accordance with DE-A 44 23 493, Example 1, without adding fluoride.

Example 3

(Fluoride-Containing Precipitated Silica with a Thickening Effect)

The process is performed in accordance with EP 0 272 380 B1, Example 1.

73 l of hot water and 5.25 l of sodium silicate solution (density 1.353 g/ml, modulus $SiO_2:Na_2O=3.46$) are heated to 85° C., with stirring, in a rubber-lined 120 (sic) precipitation vessel. 16.5 l of sodium silicate solution (composition as given above) and 1.448 l of sulfuric acid (96% strength) are simultaneously added to this alkaline precipitation mixture over the course of the next 90 minutes, while stirring and maintaining a constant temperature.

Then, the precipitated silica suspension obtained is adjusted to a pH of 3.5 with sulfuric acid (96% strength), which is achieved by allowing acid to flow in at a rate of 1.25 l/hour for a period of several minutes. The precipitated silica suspension obtained in this way has a solids content of 85.0 g/l.

The residual low-salt paste obtained after filtering and washing is converted into a sprayable suspension by intensive stirring and adding water and enough $CaF_2$ for the concentration of F to be 0.5 wt. %, with respect to the amount of silica, spray dried and milled in an air-jet mill.

Example 4

(Comparison Example, Fluoride-Free Precipitated Silica with a Thickening Effect)

The process is performed in accordance with EP 0 272 380 B1, Example 1, wherein no $CaF_2$ is added.

Toothpaste Formulations in which Precipitated Silicas in Accordance with Examples 1 to 4 are used

| | Toothpaste 1 % | Toothpaste 4 % |
|---|---|---|
| Water (deionized) | 30.60 | 31.60 |
| CMC | 1.20 | 1.20 |
| Solbrol M Na | 0.20 | 0.20 |
| Saccharin Na | 0.10 | 0.10 |
| Titanium dioxide | 0.40 | 0.40 |
| Sorbitol 70% strength | 40.00 | 40.00 |
| Silica according to Example 1 | 25.00 | 22.00 |
| AEROSIL 200 | — | 2.00 |
| Aromatic oil | 1.00 | 1.00 |
| Foaming agent | 1.50 | 1.50 |

| | Toothpaste 2 % | Toothpaste 5 % |
|---|---|---|
| Water (deionized) | 33.60 | 33.60 |
| CMC | 1.20 | 1.20 |
| Solbrol M Na | 0.20 | 0.20 |
| Saccharin Na | 0.10 | 0.10 |
| Titanium dioxide | 0.40 | 0.40 |
| Sorbitol 70% strength | 40.00 | 40.00 |
| Silica according to Example 1 | 14.00 | — |
| Silica according to Example 2 | — | 14.00 |

-continued

| | | |
|---|---|---|
| Silica according to Example 3 | — | 8.00 |
| Silica according to Example 4 | 8.00 | — |
| Aromatic oil | 1.00 | 1.00 |
| Foaming agent | 1.50 | 1.50 |

| | Toothpaste 3 % | Toothpaste 6 % |
|---|---|---|
| Water (deionized) | 39.60 | 39.60 |
| CMC | 1.20 | 1.20 |
| Solbrol M Na | 0.20 | 0.20 |
| Saccharin Na | 0.10 | 0.10 |
| Titanium dioxide | 0.40 | 0.40 |
| Sorbitol 70% strength | 40.00 | 40.00 |
| Silica according to Example 1 | 5.00 | — |
| Silica according to Example 2 | — | 5.00 |
| Silica according to Example 3 | — | 11.00 |
| Silica according to Example 4 | 11.00 | — |
| Aromatic oil | 1.00 | 1.00 |
| Foaming agent | 1.50 | 1.50 |

| | Toothpaste 7 % | Toothpaste 10 % |
|---|---|---|
| Water (deionized) | 7.95 | 12.45 |
| CMC | 0.50 | 0.50 |
| Colorant 1% strength | 0.50 | 0.50 |
| Solbrol M Na | 0.15 | 0.15 |
| Saccharin Na | 0.20 | 0.20 |
| Polyethylene glycol 400 | 3.50 | 3.50 |
| Sorbitol 70% strength | 40.00 | 40.00 |
| Glycerol | 20.00 | 20.00 |
| Silica according to Example 1 | 25.00 | 18.00 |
| AEROSIL 200 | — | 2.50 |
| Aromatic oil | 1.00 | 1.00 |
| Foaming agent | 1.20 | 1.20 |

| | Toothpaste 8 % | Toothpaste 11 % |
|---|---|---|
| Water (deionized) | 10.95 | 10.95 |
| CMC | 0.50 | 0.50 |
| Colorant 1% strength | 0.50 | 0.50 |
| Solbrol M Na | 0.15 | 0.15 |
| Saccharin Na | 0.20 | 0.20 |
| Polyethylene glycol 400 | 3.50 | 3.50 |
| Sorbitol 70% strength | 40.00 | 40.00 |
| Glycerol | 20.00 | 20.00 |
| Silica according to Example 1 | 14.00 | — |
| Silica according to Example 2 | — | 14.00 |
| Silica according to Example 3 | — | 8.00 |
| Silica according to Example 4 | 8.00 | — |
| Aromatic oil | 1.00 | 1.00 |
| Foaming agent | 1.20 | 1.20 |

| | Toothpaste 9 % | Toothpaste 12 % |
|---|---|---|
| Water (deionized) | 11.95 | 11.95 |
| CMC | 0.50 | 0.50 |
| Colorant 1% strength | 0.50 | 0.50 |
| Solbrol M Na | 0.15 | 0.15 |
| Saccharin Na | 0.20 | 0.20 |
| Polyethylene glycol 400 | 3.50 | 3.50 |
| Sorbitol 70% strength | 40.00 | 40.00 |
| Glycerol | 25.00 | 25.00 |
| Silica according to Example 1 | 5.00 | — |
| Silica according to Example 2 | — | 5.00 |
| Silica according to Example 3 | — | 11.00 |
| Silica according to Example 4 | 11.00 | — |
| Aromatic oil | 1.00 | 1.00 |
| Foaming agent | 1.20 | 1.20 |

Determining the Fluoride Release Dynamics as a Measure of the Deposition Effect and the pH as a Function of Time using the Precipitated Silica in accordance with Example 1

See also FIG. 1 (Fluoride release dynamics) and FIG. 2 (pH dynamics), with respect to the data in the Table below.

| | Amount of fluoride with respect to precipitated silica | pH |
|---|---|---|
| After 2 min. | 0.479 ppm | 7.95 |
| After 5 min. | 0.767 ppm | 7.91 |
| After 15 min. | 1.62 ppm | 7.71 |
| After 30 min. | 2.24 ppm | 7.59 |
| After 45 min. | 2.86 ppm | 7.42 |
| After 60 min. | 3.62 ppm | 7.29 |
| After 120 min. | 4.64 ppm | 7.09 |
| After 150 min. | 5.08 ppm | 7.01 |
| After 180 min. | 5.28 ppm | 6.96 |
| After 240 min. | 5.48 ppm | 6.91 |
| After 300 min. | 5.73 ppm | 6.87 |
| After 360 min | 5.80 ppm | 6.84 |
| After 24 hours | 7.09 ppm | 6.86 |
| After 25 hours | 7.06 ppm | 6.79 |
| After 26 hours | 6.89 ppm | 6.75 |
| After 48 hours | 7.64 ppm | 6.73 |
| After 49 hours | 7.49 ppm | 6.69 |
| After 50 hours | 7.43 ppm | 6.67 |
| After 51 hours | 7.40 ppm | 6.65 |

Calculation used for Table given above:

| | | |
|---|---|---|
| Total fluoride in test suspension | [F$^-$] tot. | 50 ppm |
| Soluble fluoride | [F$^-$] sol. | 7.8 ppm |
| Released fluoride | [%] of sol. F$^-$ | 97.9 |

The silica according to the invention in accordance with Example 1 has a fluoride deposit of 5 mg F$^-$/g of silica, corresponding to 50 ppm in the test suspension. Based on the solubility product of $CaF_2$, 7.8 ppm of that is soluble. The experiment demonstrates that 97.9% of the soluble fluoride is released within 2 days.

Determining the Total Fluoride Content of the Silica

The total fluoride content of the silica is determined using pyrohydrolysis and ion chromatography.

| Silica | Experimental result [%] |
|---|---|
| in accordance with Example 1 | 0.51 ± 0.02 |

The result shows that the theoretical total amount of fluoride used, 5 mg F per g of precipitated silica (0.5 wt. %) is fixed on the precipitated silica.

Cleaning Test on Molar Teeth and Analysis of the Surface using XPS/SIMS

Using precipitated silica according to the invention, in accordance with Example 1, it is shown that fluoride ions are stored on the surface of the tooth after a single cleaning process.

| Parameter | Tooth no. 1 | Tooth no. 2 | Tooth no. 3 |
|---|---|---|---|
| Polishing | Tooth surface is polished | Tooth surface is polished | Tooth surface is polished |
| 1st surface analysis | Analysis by means of | Analysis by means of | Analysis by means of |

-continued

| Parameter | Tooth no. 1 | Tooth no. 2 | Tooth no. 3 |
|---|---|---|---|
| (= initial status before cleaning) | XPS/SIMS | XPS/SIMS | XPS/SIMS |
| Preparation of toothpaste/ cleaning material suspensions | A suspension of Colgate caries preventive toothpaste is homogenised 1:1 in water | A standard paste A containing 20% of silica in accordance with Example 1 is dispersed 1:1 in water | A standard paste B containing 20% of silica in accordance with Example 2 and 1000 ppm of $CaF_2$ is dispersed 1:1 in water |
| Cleaning process | Cleaned for 5 min. with electric toothbrush on a vibrating table | Cleaned for 5 min. with electric toothbrush on a vibrating table | Cleaned for 5 min. with electric toothbrush on a vibrating table |

X-Ray Photoelectron Spectrometry (XPS)

The XPS technique, which is based on the principle of a photoelectronic effect [1–4], is used in order to determine the surface composition of the teeth before and after treatment with fluoride. Due to the high surface specificity of XPS, the processes in the outermost few nanometers, the boundary region in which the incorporation of F and chemical attack on the enamel or abrasive processes take place, are analyzed specifically.

Analysis covers only the outermost layers of atoms, that is selectively within the region in which the incorporation of fluoride or the elution of fluoride takes place. Although analysis penetrates into the material only to the depth of a few atomic layers, the "analysis spot" is passed specifically over the entire tooth so that the effect of microinhomogeneities on the analytical results can be excluded, and relevant, macroscopic data is obtained for the entire tooth surface. Thus, the XPS method is more surface-sensitive, by a factor of about 1000, than the EDX (energy dispersive X-ray analysis) technique used in electron microscopy.

The XPS method offers the advantage of effective quantifiability. In particular it also provides data relating to the chemical bonding status of the surface of the enamel or dentine. XPS is therefore an internationally recognized method of measurement in dental research and in dental clinics (in particular in the USA) for following the complexing behaviour of Ca, the Ca/P ratio in the surface of the tooth or dentine and effects due to cleansers and primers.

Principle:

1. Insertion

A molar tooth is inserted into the XPS test unit (Leybold LHS12) without any further pre-treatment. The equipment used consists of several vacuum chambers. In the first chamber, the molar tooth is carefully taken from atmospheric conditions to pre-vacuum conditions (about $10^{-2}$ mbar, oil-free rotary disc-type pump vacuum) in order to pump off moisture and other, possibly organic, readily desorbable constituents, in particular from the dentine. Then the roughly pre-dried tooth is transferred to a preparation chamber. In this chamber, the material is pumped down to high or ultra-high vacuum conditions ($10^{-7}$–$10^{-8}$ mbar, turbopump vacuum). During this time, a residual gas quadrupole mass spectrometer is used to test whether volatile residual components (in particular water) are still escaping from the material under these extreme conditions. The pumping down processes take place exclusively at room temperature. Thus, the tooth is not stressed in any other way. The sample conditioned in this way is finally transferred to the actual analysis chamber (base pressure: $6$–$8 \times 10^{-10}$ mbar, turbopump, getter-ion pump and Ti sublimation pump vacuum).

2. Measuring process

The surface of the tooth is bombarded with soft X-radiation ($MgK_\alpha$ radiation, 1253.6 electron volts, power 200 watts) over its entire surface, under ultra-high vacuum conditions. This triggers photoemission processes. Electrons are released (e.g. F1s, Ca2p, P2s, C1s, O1s, etc.). Photoelectrons which have only a very short mean free path in solids are emitted due to the stimulation energy selected. Thus, the method is specific to the region in the uppermost layers of atoms, i.e. in the case of oxidic minerals such as e.g. hydroxyapatite/fluoroapatite, the uppermost 2 nanometers are selectively involved.

Only the electrons which are emitted directly at the surface of the material can leave the material and act as data carriers. The kinetic energy of these emitted electrons is determined using a hemispherical energy analyzer (CHA, Leybold EA11A). The bonding energy of the photoelectrons removed from the surface atoms of the tooth is measured from the difference between the energy measured and the energy of the irradiated X-ray photons. Despite the high surface specificity, about 1.5 cm$^2$ of the surface area can be calibrated and analysed by integration using optical microscopy and an adjustment laser. The effect of microinhomogeneities is thus averaged out.

3. Evaluation

1. Surface concentrations

The XPS spectra measured are first processed by polynomial fits and subtraction programs to remove so-called X-ray satellite signals. Then all the elements detected by XPS (except H and He) are identified. Quantification is performed after background subtraction using Shirley's method [5] taking into account the element-specific relative sensitivity factors.

2. Bonding states

On the basis of the bonding energy values, it can also be determined in which chemical bonding state the elements are present. Thus, for instance, carbonate carbon and aliphatically bonded carbon can be differentiated on concrete etc. For more than a qualitative evaluation of this important aspect, the sample-specific electrostatic charge on the electrically poorly conducting material has to be taken into account by means of internal reference procedures or compensation techniques.

LITERATURE

[1] K. Siegbahn et. al., Nova Acta Reg. Soc. Sci. Ups. Ser. IV vol. 20 (1967)

[2] Practical Surface Analysis, Ed. D. Briggs, M. P. Seah, Second Edition, 1990, John Wiley, Chichester and Salle+ Sauerländer, Aarau

[3] J. F. Moulder, W. F. Stickle, P. E. Sobol, K. D. Bomben, Handbook of X-ray Photoelectron Spectroscopy, Ed. J. Chastain, Perkin Elmer, Physical Electronics Division, Eden Prairie, Mich., USA, 1992

[4] R. Holm, S. Storp, Methoden zur Untersuchung von Oberflächen, Ullmanns Enzyklopädie der technischen Chemie, vol 5, Verlag Chemie, Weinheim, 1980, pp. 242–256

[5] D. A. Shirley, Phys. Rev. B 5, 1992, 4709

Formulations of the 'Riefenwert' Standard Pastes used

| Raw materials | Standard paste A [%] | Standard paste B [%] |
|---|---|---|
| 1 Demineralized water | 34.54 | 34.54 |
| 2 CMC, Blanose 7 MCF | 1.00 | 1.00 |

-continued

| Raw materials | Standard paste A [%] | Standard paste B [%] |
|---|---|---|
| 3 Preservative, Solbrol M | 0.20 | 0.20 |
| 4 Sweetener, saccharin | 0.10 | 0.10 |
| 5 $CaF_2$ | — | 0.21 |
| 6 Paraffin oil | 0.50 | 0.50 |
| 7 Sorbitol | 40.00 | 40.00 |
| 8 Aromatic oil | 1.00 | 1.00 |
| Silica | 20% precipitated silica acc. to Example 1 | 20% precipitated silica acc. to Example 2 |

Preparing Standard Pastes A and B

After swelling the binder (CMC) in water in Retsch mill RM1, components 3 to 8 are mixed in and homogenized. 160 g of the mixture obtained are weighed out each time and 40 g of the particular precipitated silica according to Example 1 or 2 are added each time, with the Retsch mill operating. After complete incorporation of the precipitated silica, the pastes are then homogenized three times on a precision triple roll mill.

Preparing the Toothpaste/Cleanser Suspension

Then, standard pastes A and B and Colgate Bifluoride are each diluted 1:1 with water and dispersed in a 400 ml beaker for 5 min using a double-blade stirrer at 1500 rpm.

Describing the Cleaning Process

The silica-containing toothpaste suspensions are placed in the cleansing apparatus and the human teeth (molars), polished on the chewing surface, are cleaned with an electric toothbrush (tradename Broxodent). The vibrating table used for the cleaning equipment was adjusted to 60 vibrations/min. in order to avoid sediment production. After the cleaning process, the teeth are rinsed under flowing, fluoride-free water, dried and the surface examined analytically.

In the comparison trials, the commercially available toothpaste Colgate Bifluoride was also tested.

Test Results

Surprisingly, these results can be used to show that the silica according to the invention from Example 1 in standard paste A causes a significantly higher deposition of fluoride after a single cleaning process than standard paste B, in which the abrasive silica and $CaF_2$ are added separately, and Colgate Bifluoride, a toothpaste with a propagated long-term effect which contains NaF, NaMFP and calcium. This means that it would be expected that an improvement in resistance of the tooth to demineralization would be produced. At the same time, the fluoride release dynamics described under 1 suggest that delayed release of the fluoride takes place over several days in vivo at 37° C. Colgate toothpaste with bifluoride and calcium is commercially available. It has the following ingredients (according to CFTA):

dicalcium phosphate, water, glycerol, sorbitol, cellulose gum, sodium lauryl sulfate, flavoring, tetrasodium pyrophosphate, sodium saccharin, sodium monofluorophosphate, sodium fluoride.

Determining the Fluoride Release Dynamics of Silicas Doped with Alkali Metal and Alkaline Earth Metal Fluorides 1) Basic principles The fluoride release of fluorine-containing silicas is tested over time when using this method. Thus, it can be determined whether the silica has a deposition effect or not.

Ion-selective electrodes and an ion analyzer are used for the measurements. Alkali metal and alkaline earth metal salts, for example, are used for fluoride doping.

2) Equipment and reagents 2.1) Equipment

Analytical scales, Sartorius A 200 S
Spatula
250 ml plastic screw-topped container
Ika magnetic stirrer, ES 5, with 2 cm stirring rod
Colora thermostat with water bath
ORION pH/mV and ion meter Model EA 940
with pH electrode
with ion-selective electrode

|  | Tooth 1 Colgate Bifluoride | Tooth 1 Colgate Bifluoride | Tooth 2 Standard paste A | Tooth 2 Standard paste A | Tooth 3 Standard paste B | Tooth 3 Standard paste B |
|---|---|---|---|---|---|---|
| Condition of human tooth, chewing surface | polished | cleaned | polished | cleaned | polished | cleaned |
| Surface percentage of fluoride, 1st measurement | 0.68 | 1.04 | 0.45 | 0.91 | 0.46 | 0.69 |
| Δ percent, 1st measurement | +0.36 | | +0.46 | | +0.23 | |
| Repeat measurement | | | | | | |
| Condition of human tooth, chewing surface | polished | cleaned | polished | cleaned | polished | cleaned |
| Surface percentage of fluoride, 2nd measurement | 0.33 | 0.75 | 0.41 | 0.91 | 0.35 | 0.33 |
| Δ percent, 2nd measurement | +0.42 | | +0.50 | | −0.02 | |

2.2) Reagents

> Distilled water
> ORION fluoride standard solution 100 ppm
> to prepare the following calibration solutions:
> 100 ppm
> 50 ppm
> 20 ppm
> pH buffer solutions; pH 4.0, 7.0 and 10.0

3) Safety aspects:
> NaF is toxic
> R 23/24/25    S 1/2-26-44
> in acid pH, the HF evolved is very toxic
> R 26/27/28-35    S 2/9-26-36/37-45

4) Experimental details 4.1) Making up the fluoride calibration solutions

The ORION fluoride standard provided, 100 ppm, is diluted 1:1 or 1:5 with distilled water for calibration purposes and is stored in a 250 ml plastic screw-topped container.

4.2) Standardizing

The ion meter is calibrated before the start of each set of experiments. The calibration and buffer solutions mentioned above are used for this purpose. The electrode is rinsed with distilled water and carefully dried before it is immersed in a calibration solution. The information provided by the manufacturer of the equipment should be observed when doing this.

4.3) Measurements 100 g of a 1% strength silica/water suspension is weighed accurately to 10 mg into a 250 ml plastic screw-topped container. In order to prevent contact with any hydrofluoric acid evolved, the experiments should be performed in a fume cupboard.

The suspension is held at a constant 37° C. on a water bath and stirred with a magnetic stirrer set at stirring speed 3.

The release of fluoride is measured using an ion-selective electrode. For this, the membrane in the ion-selective electrode is rinsed with the solution contained in the electrode, in accordance with the manufacturer's information, and the level is then made up to the correct level again. The electrode is rinsed with distilled water and dried with a soft cloth, the tip of the electrode is immersed in the suspension and the fluoride concentration is read in ppm, with stirring, at specific intervals of time and recorded. The measurement intervals are increased from 2 min to several hours until the experimental value remains constant.

At the same time, the pH of the suspension is measured. The electrode is rinsed with distilled water and dried before the measurement is made. The ion analyser is then switched over to pH measurement. The electrode is immersed in the suspension and the pH is measured, with stirring, and recorded.

The electrodes remain in the suspension for further measurements of fluoride concentration and pH. It is simply a matter of switching over to the particular type of electrode and then reading the experimental value.

5) Evaluation

Figure 2:
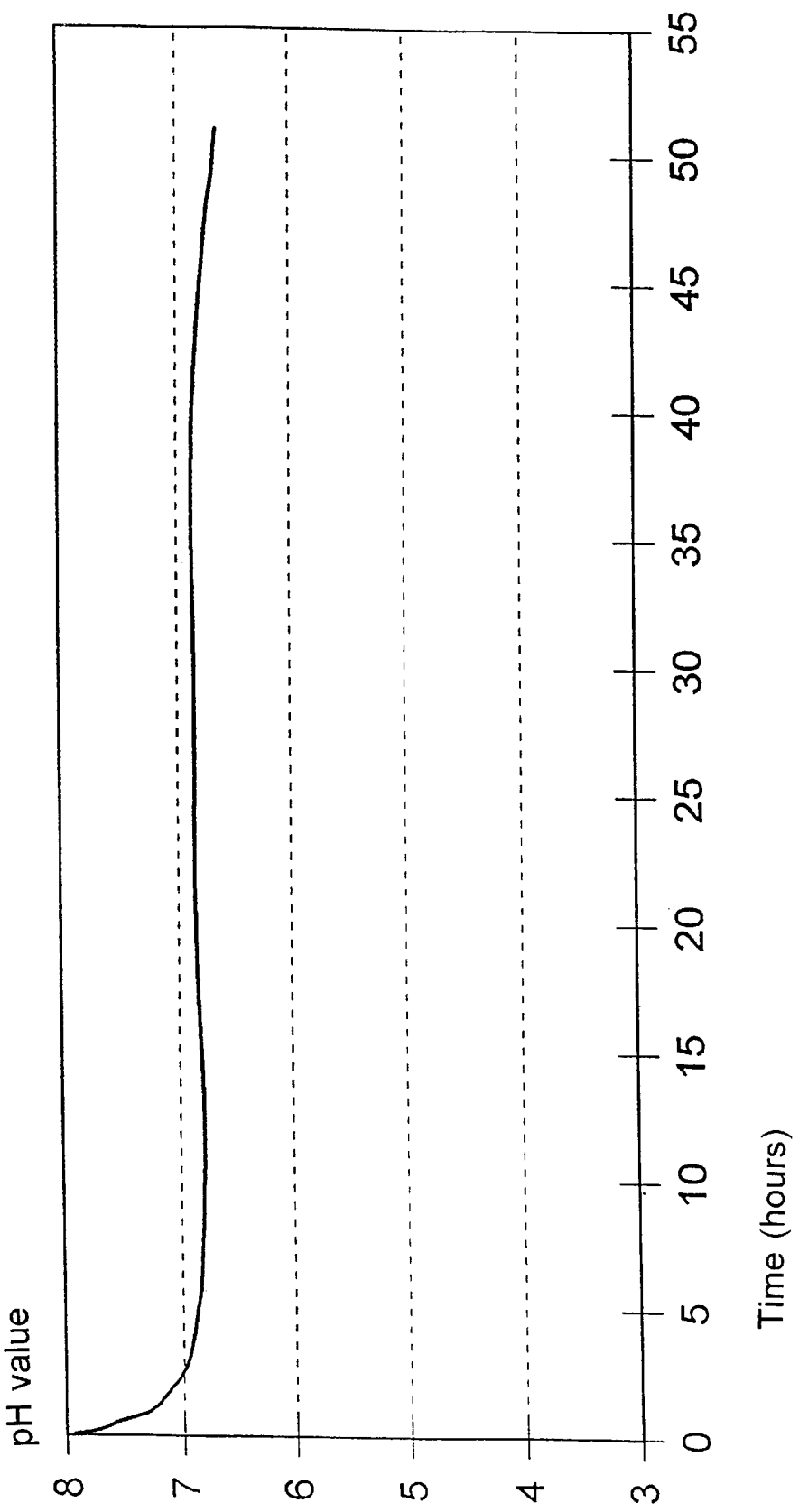
FIG. 2 shows, graphically, the relationship between pH and time, for silica according to Example 1.

The fluoride release dynamics are depicted graphically in FIG. 1 as fluoride concentration against time, and in FIG. 2 as pH against time.

The following data are recorded on the results sheet:

1) the fluoride concentration recorded after achieving the equilibrium state, with the corresponding time, $[F]_{eq}$ in ppm;

2) theoretical fluoride concentration from 1 g of silica per 100 g of suspension, $[F]_{tot}$ in ppm;

3) concentration of soluble fluoride from 1 g of silica per 100 g of suspension, $[F]_{sol}$ in ppm; and 4) data on fluoride concentration recorded, $[F]_{eq}$, as a percentage of the concentration of soluble fluoride, $[F]_{sol}$.

The results show that it is possible to produce a fluoride-doped precipitated silica which has the same application-oriented properties as the reference precipitated silica without fluoride but which has the required deposition effect. Further examples show that abrasive silicas, thickening silicas and bifunctional silicas can be used as active substance carriers in accordance with the invention.

Example 3 may be mentioned as a representative example which is coated using variant 4 and whose deposition effect can also be detected.

While the invention has been described above with respect to certain embodiments thereof, variations and modifications may be made without departing from the spirit and scope of the invention.

What is claimed is:

1. A precipitated silica containing an active substance, having delayed release of the active substance over a period of about two days.

2. A precipitated silica according to claim 1, wherein the active substance comprises fluoride ions.

3. A process for preparing a precipitated silica containing an active substance according to claim 1, comprising:

adding the active substance, which is moderately to sparingly soluble in water, to a precipitation vessel or to a precipitated suspension during preparation of the precipitated silica; and recovering the precipitated silica containing the active substance.

4. A process for preparing a precipitated silica containing an active substance according to claim 1, comprising:

washing and optionally redispersing the precipitated silica;

adding the active substance; and drying the active substance, which is moderately to sparingly soluble in water, together with the washed and optionally redispersed precipitated silica.

5. A process for preparing a precipitated silica containing an active substance according to claim 1, comprising:

drying the precipitated silica; and milling the active substance, which is moderately to sparingly soluble in water, together with the dried precipitated silica.

6. A process for using a precipitated silica containing an active substance according to claim 1 comprising:

incorporating the precipitated silica containing an active substance in oral hygiene agents.

7. A process for using a precipitated silica containing an active substance according to claim 6 comprising:

releasing fluoride ions from the oral hygiene agents in which the precipitated silica containing the active substance is incorporated.

* * * * *